United States Patent [19]
Martin et al.

[11] Patent Number: 6,048,200
[45] Date of Patent: Apr. 11, 2000

[54] SINGLE USE NOZZLE FOR DENTAL SYRINGE

[76] Inventors: Daniel H. Martin; Todd E. Davis, both of 757 SE. 17th St. #383, Fort Lauderdale, Fla. 89123

[21] Appl. No.: 08/934,777

[22] Filed: Sep. 22, 1997

[51] Int. Cl.[7] .................................... A61G 17/02
[52] U.S. Cl. .................................................. 433/80
[58] Field of Search ................................... 433/80

[56] References Cited

U.S. PATENT DOCUMENTS

| | | | |
|---|---|---|---|
| 4,026,025 | 5/1977 | Hunt | 433/80 |
| 4,820,152 | 4/1989 | Warrin et al. | 433/86 |
| 4,975,054 | 12/1990 | Esrock | 433/80 |
| 4,993,941 | 2/1991 | Maita et al. | 433/80 |
| 5,049,071 | 9/1991 | Davis et al. | 433/80 |
| 5,252,064 | 10/1993 | Baum et al. | 433/80 |
| 5,433,485 | 7/1995 | Austin, Jr. et al. | 433/80 |
| 5,616,028 | 4/1997 | Hafele et al. | 433/80 |

Primary Examiner—John J. Wilson

[57] ABSTRACT

A disposable nozzle for a dental syringe is disclosed comprising an inner tube and an outer tube. The outer tube is constructed with depressions for inner tube retention. The depressions also serve as indicia. The proximal end of the outer tube has at least one indentation across its radius to prevent blockage of media flows.

10 Claims, 2 Drawing Sheets

SINGLE USE NOZZLE FOR DENTAL SYRINGE

BACKGROUND OF THE INVENTION

1. Field of the Invention

In common use in the dental profession are three way syringes for discharging pressurized air and water flows into the mouth. Such devices typically include a discharge nozzle which is detachable because of the necessity to sterilize or replace it before use with a new patient. Commonly, the nozzle is replaced after each use, because of the expense and difficulty of sterilization.

The nozzle commonly consists of an inner tube and a concentric outer tube. The present invention relates to the retention of the inner tube within the outer tube. This retention is necessary to maintain the separation of air and water as they flow from the syringe head into the passageways in the discharge nozzle. The separation of air and water is important for dental procedures which require air, but during which no water can be present. The retention of the inner tube also helps to ensure a mist when the practitioner desires both air and water.

The invention also relates to the prevention of media blockage as media flows into the nozzle.

2. Description of the Prior Art

As shown in U.S. Pat. Nos. 4,248,589; 5,242,300; 5,342,195; and 5,433,485; commonly, dental syringes utilize an O-ring to maintain separation of air and water. This 0-ring can fail to maintain separation of air and water if the nozzle is not completely inserted into the syringe, or if the inner tube is not retained at a predetermined placement within the outer tube.

U.S. Pat. Nos. 4,248,589; and 5,433,485 retain the inner tube, but in so doing close off the air passageway, and therefore utilize a groove about the outer tube and a new hole in the side of the outer tube. This increases manufacturing costs and the retail price, and therefore decreases the likelihood that the practitioner will replace the nozzle after a single use. U.S. Pat. No. 5,433,485 provides for an indicium with the intent that it will be obscured when the nozzle is properly inserted into the syringe. However, if the nozzle is used with the syringes of other manufacturers, the indicium may not be located at the appropriate location in relation to the various syringes.

U.S. Pat. No. 5,342,195; in the embodiment shown in FIGS. 10–11, requires a press fit of the two components, which would tend to increase manufacturing costs.

U.S. Pat. No. 5,242,300 utilizes an oblique end face at the proximal end of the outer tube to prevent media blockage. An oblique end face would be very difficult to chamfer, which decreases the likelihood that it will be utilized in manufacture.

SUMMARY OF THE INVENTION

The present invention provides for a dental syringe discharge nozzle with an inner tube and a concentric outer tube. The inner tube provides a conduit for a first media, typically water, and the space between the inner tube and outer tube provides a conduit for a second media, typically air. The outer tube is compressed about the inner tube, forming multiple depressions on the outer tube which hold the inner tube in place. The placement of the depressions allows each one to serve as an indicium, so that one or more will be hidden when the nozzle is properly inserted into the dental syringe. The usage of multiple depressions is implemented with the intent that the nozzle can be utilized in the dental syringes of various manufacturers and still have at least one indicium at the appropriate placement in relation to the syringe.

The proximal end of the outer tube is constructed with at least one indentation across its radius, ensuring that air flows are not blocked. The usage of an indentation in the proximal end of the outer tube provides for a symmetrical end face that does not impede the production of a chamfer. The inner and outer tubes are chamfered or radiused at both ends. The nozzle is bent approximately one inch from the distal end to assist the direction of media flows in the desired direction.

One advantage which may not at first be apparent is that the retention of the inner tube is accomplished with easy-to-produce dimples, which together with the other features of the invention, provides for very low manufacturing costs. The intent is that the nozzle will be sufficiently affordable that every dental practitioner will replace it after use with a patient, therefore preventing the possibility of cross contamination between patients.

BRIEF DESCRIPTION OF THE DRAWINGS

Advantageous modifications and features of the invention can now be readily ascertained from the following detailed description thereof, taken in conjunction with the accompanying drawings; in which.

DETAILED DESCRIPTION

Figure 1:
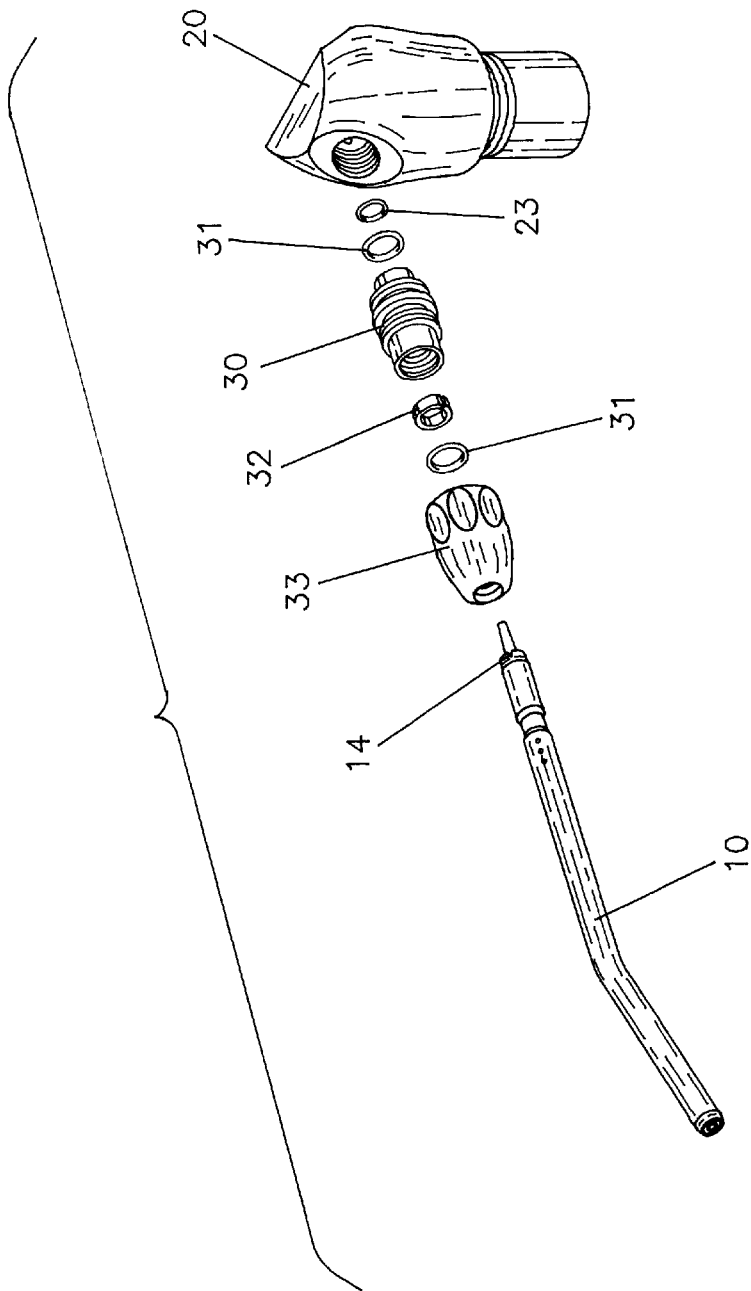
FIG. 1 is a perspective view of a dental syringe nozzle retention assembly, incorporating the inventive dental syringe discharge nozzle.
Figure 2:
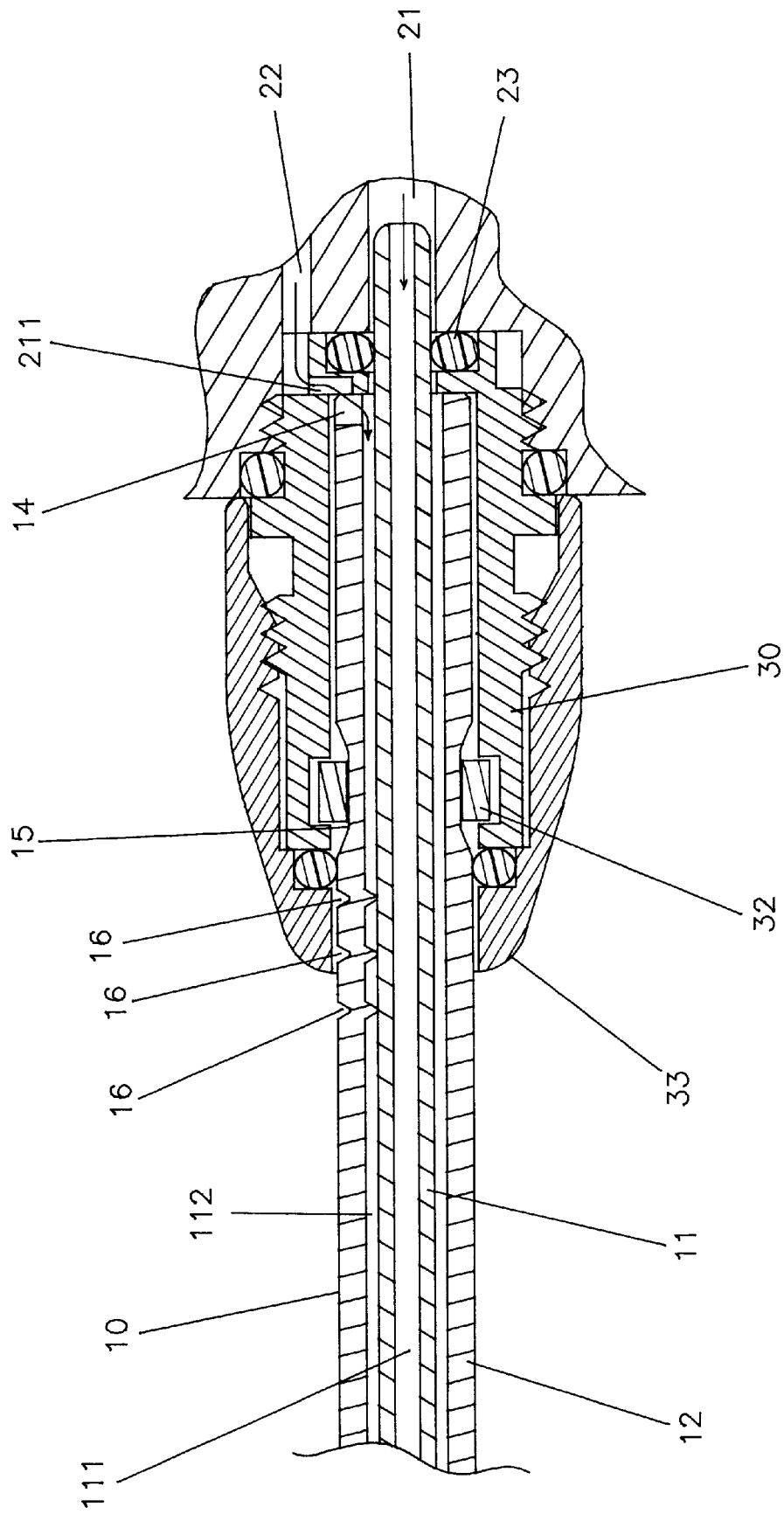
FIG. 2 illustrates on an enlarged scale a sectional view of a dental syringe nozzle retention assembly, incorporating the inventive nozzle.

The illustrated dental syringe nozzle retention assembly consists of a syringe head 20, to which a retention coupler 30 is threadedly attached, a retention snap ring 32 captivated within the coupler 30, a retention nut 33 which is threadedly attached to the coupler 30, and sealing O-rings 23, 31.

The first media, typically water, flows from syringe head passageway 21, and is discharged through the nozzle inner tube center passageway 111.

The second media, typically air, flows from syringe head passageway 22, through the adapter side bore 211, through nozzle radial indentation 14, and then is discharged from the syringe through the concentric nozzle passageway 112.

The discharge nozzle 10, is retained by the snap ring 32, which is captivated within the coupler 30. When the nozzle 10 is fully inserted into the coupler 30, the snap ring 32 is pressed outward, exerting pressure on the retaining groove 15 to hold the nozzle 10 in place.

The inner tube 11 of the nozzle is retained in place by one or more outer tube depressions 16, formed by compressing the outer tube 12 about the inner tube 11. This prevents movement of the inner tube 11, ensuring that the inner tube is pushed through the sealing O-ring 23 when the dental practitioner pushes the nozzle 10 into the nozzle retention assembly. The outer tube depressions 16 are placed so that they can each serve as an indicium: One or more will be covered by the retaining nut 33 when the nozzle 10 is inserted completely into the retention assembly. The use of more than one indicium provides that, when the nozzle is used with a wide variety of syringes from other manufacturers, one indicium will be in the appropriate location in relation to the syringe used. Therefore, the dental practitioner inserts the nozzle 10 into the dental syringe until it is properly seated, and then notes the relationship of the depressions 16 to the nozzle retention assembly. One or more indicia will likely be visible, so that the practitioner can tell at a glance whether the nozzle is properly inserted before using it with a patient.

References herein to the details of the illustrations are by way of example only and not intended to limit the scope of the claims which themselves recite those details regarded as important to the invention.

What is claimed is:

1. A dental instrument assembly comprising:
    a) an instrument body with two media passageways therein;
    b) a nozzle retention system;
    c) a nozzle comprising:
        1) an inner tube to provide a conduit for a first media;
        2) a concentric outer tube providing a conduit for a second media; and
        3) a depression constructed in the outer tube that extends against the inner tube to retain it, said depression located to be hidden from view whenever the nozzle is connected properly with the nozzle retention system and instrument body.

2. The dental instrument assembly of claim 1 wherein said outer tube is constructed with a retaining groove perpendicular to the passageway of said outer tube.

3. The dental instrument assembly of claim 1 wherein said outer tube is constructed with a chamfer or radius at the proximal and distal ends.

4. The dental instrument assembly of claim 1 wherein said inner tube is constructed with a chamfer or radius at the proximal and distal ends.

5. The dental instrument assembly of claim 1 wherein said nozzle is bent approximately one inch or less from the distal end.

6. A dental instrument assembly comprising:
    a) an instrument body with two media passageways therein;
    b) a nozzle retention system;
    c) a nozzle constructed with two or more indicia, located so that at least one indicium is hidden from view just inside the most distal nozzle retention system component when the nozzle is connected properly with the nozzle retention system and instrument body.

7. The dental instrument assembly of claim 6, wherein at least one indicium remains visible when the nozzle is connected properly with the nozzle retention system and instrument body.

8. The dental instrument assembly of claim 6, wherein at least one indicium is composed of a depression constructed in the outer tube that extends against the inner tube.

9. A dental instrument nozzle comprising:
    a) an inner tube to provide a conduit for a first media;
    b) a concentric outer tube providing a conduit for a second media; and
    c) two or more depressions constructed in the outer tube that extend against the inner tube to retain it, each depression located to be hidden from view whenever the nozzle is connected properly with at least one model of dental instrument.

10. The dental instrument assembly of claim 9, wherein each depression is spaced longitudinally apart.

* * * * *